United States Patent [19]

Fischer et al.

[11] Patent Number: 4,591,639
[45] Date of Patent: May 27, 1986

[54] MICROBIAL POLYSACCHARIDE AMINE ADDUCTS

[75] Inventors: Edgar Fischer, Frankfurt am Main; Hartmut Voelskow, Hattersheim am Main, both of Fed. Rep. of Germany

[73] Assignee: Hoechst Aktiengesellschaft, Fed. Rep. of Germany

[21] Appl. No.: 522,608

[22] Filed: Aug. 12, 1983

[30] Foreign Application Priority Data

Aug. 14, 1982 [DE] Fed. Rep. of Germany ....... 3230303

[51] Int. Cl.$^4$ ............................................. C08B 37/00
[52] U.S. Cl. ................................... 536/114; 252/315.3; 252/194
[58] Field of Search ................................ 536/127, 114

[56] References Cited

U.S. PATENT DOCUMENTS 3,422,085  1/1969  Gill et al. .......................... 536/127
4,254,257  3/1981  Schroeck .......................... 536/114

*Primary Examiner*—Johnnie R. Brown
*Attorney, Agent, or Firm*—Finnegan, Henderson, Farabow, Garrett & Dunner

[57] ABSTRACT

Microbial polysaccharides can be quantitatively precipitated from their aqueous solutions, in particular directly from the fermentation solutions, in an acidic medium in the form of an adduct with a tertiary amine which has a long-chain alkyl radical. It is advantageous to add the amine to the polysaccharide solution and then to carry out the precipitation, in particular by adding the dispersion obtained to an acidic coagulation bath. The adducts are suitable for use as thickeners and for preparing the free polysaccharides.

2 Claims, No Drawings

MICROBIAL POLYSACCHARIDE AMINE ADDUCTS

The invention relates to a process for isolating microbial polysaccharides from their aqueous solutions by precipitating them in an acidic medium in the form of an adduct with a long-chain alkylamine, to the adducts thus obtained and to their use.

Owing to their excellent properties, fermentationproduced extracellular microbial polysaccharides are used in industry as thickeners, gelling or suspending agents, protective colloids or water-binding agents. Their method of preparation makes these products fairly expensive, one contributing factor to their high price being the existing, technically complicated methods of isolating them.

U.S. Pat. No. 3,928,316 discloses the isolation of the anionic heteropolysaccharide obtained by fermentation with the aid of the bacterium Xanthomonas campestris NRRL B-1459 in the form of a water-insoluble salt of a primary long-chain amine from the acidified dilute fermentation solutions. In this process, the fatty amine is used in such an amount that all the carboxyl groups of the polymer are converted into amine salts. Besides the fact that the fermentation medium needs to be diluted, thus necessitating a correspondingly complicated working-up procedure, the process has the disadvantage that the solid fatty amine needs to be used in the form of a water-soluble salt. If the process is carried out at temperatures above the melting point of the free amines, the xanthan is more or less strongly modified, since acetyl groups bonded in the form of esters react to give amide groups.

The published British Patent Application No. 2,053,945 describes a similar process where a polyamine is used to precipitate the polysaccharide. In this process the fermentation broth has to be substantially diluted also. In the event that it is intended to isolate the amine from the amine salt, this patent application gives a method whereby the dry salt is treated with a solution of a strong base in a liquid which does not dissolve the free acidic polysaccharide, such as aqueous methanol.

U.S. Pat. No. 3,119,812 discloses a method wherein the polysaccharide formed by Xanthomonas campestris NRRL B-1459 is precipitated with quaternary ammonium salts from the dilute fermentation broths. In this method, it is necessary either to dilute the fermentation broths to a considerable extent or to add alkali metal chlorides, in order to precipitate the polysaccharide quantitatively. At least 0.8 part by weight of ammonium salt is used per part by weight of polysaccharide. The resulting amine adducts are very stable, and to cleave them they need to be repeatedly treated with methanol containing potassium chloride, the potassium salt being obtained as a result of the treatment. An additional operation is necessary to prepare the free xanthan.

We have now found a process for isolating microbial polysaccharides from their aqueous solutions by precipitating them in an acidic medium in the form of an adduct with a long-chain alkylamine, which comprises using an amine of the formula $$NR^1R^2R^3$$

in which $R^1$ is alkyl having 10–20 carbon atoms, and $R^2$ and $R^3$, which are identical or different, denote methyl or ethyl.

We found, surprisingly, that the tertiary amines used according to the invention eliminate the need to dilute the fermentation solutions or to add salt, which considerably simplifies the working-up. In addition use of amines which are liquid at room temperature may permit some preferred embodiments of the process, which are described in detail below.

Preferred tertiary amines for the process according to the invention are:

decyldimethylamine, octadecyldimethylamine, dodecyldimethylamine, undecyldimethylamine tetradecyldimethylamine, eicosyldimethylamine, hexadecyldimethylamine, undecyldiethylamine and heptadecyldimethylamine, dodecylmethylethylamine.

The easily accessible fatty dimethylalkylamines, in particular the technical products, the long alkyl radical of which is derived from oils and fats, such as coconut fat, soybean oil or tallow fat, are particularly preferred. It is immaterial if these technical products contain small amounts of alkenyl compounds. In other words, it is not necessary for the corresponding raw materials or amines to be fully hydrogenated. It is thus also possible to use technical crude products, which helps to cheapen the process according to the invention.

The process is suitable for isolating any microbial extracellular polysaccharide which has acidic groups. Examples of microorganisms required for this purpose are listed in the abovementioned British Patent Application No. 2,053,945, in the table on pages 1–3. Of industrial interest are the heteropolysaccharides which are formed by fermentation with the aid of bacteria of the Xanthomonas genus. Examples of representative strains thereof are X. begoniae, X. carotae, X. hederae, X. incari, X. malvacearum, X. phaseoli and, in particular, X. campestris. The heteropolysaccharide formed in particular by the strain Xanthomonas campestris NRRL B-1459 and containing glucose, mannose and glucuronic acid units in the polymer molecule, and which also carries acetyl and pyruvic acid groups, is also referred to as xanthan. The preparation of this product, and of similar resins, is described in British Patent Application No. 2,053,945, U.S. Pat. No. 3,406,114 quoted therein, and U.S. Pat. No. 3,928,316.

These fermentation methods give a solution which contains about 0.5 to 4% by weight of resin. In the case of xanthan, it is advisable to select as a starting material fermentation broths containing about 1.8 to 2% by weight.

In a preferred embodiment of the invention, the crude fermentation broth is mixed directly with the liquid tertiary amine. In general, this does not give a precipitate, which has the advantage that the dispersion formed can be transported without difficulties, for example, into a coagulation bath where the adduct is precipitated in a form suitable for further processing; for example in the form of a filament, tape, strand or globules.

If desired, it is possible, in the abovementioned or any other embodiment of the invention, to heat the tertiary amine together with the fermenter broth at more or less elevated temperatures for a longer or shorter period without the polymer being damaged.

The amount of amine required can vary within wide limits, and it depends on the nature of the polymer and on the remaining constituents of the fermenter broth. The optimum amount can be easily determined by means of a simple preliminary experiment. In general, a quantitative precipitation is achieved with about 5–80% by weight, preferably 10–40% by weight, relative to the polysaccharide. Higher quantities of amine can be used without disadvantage, but they do not produce any further benefit.

The amount of amine can be kept particularly low if the amine-containing polymer suspension is added to an acidic coagulation bath which contains an amount of the amine, preferably less than half.

The polymer is percipitated in an acidic medium, namely a pH range from about 2 to 6.5, preferably 3.5 to 6.0, in particular 4.0–5.5. Organic acids are advantageously used to set this pH range. The preferred organic acids are low molecular weight monocarboxylic acids having up to 5 carbon atoms and which can also carry hydroxyl groups, such as, for example, formic acid, acetic acid, propionic acid, glycolic acid or lactic acid. Acetic acid is best, since the coagulation bath solutions can be regenerated by simple distillation.

Regardless of whether the acid is added to the fermentation broth, to effect the precipitation, or whether it is already present in the form of a coagulation bath, it is advantageously initially to admix the amine to the fermenter broth, since the resulting adducts have a very homogeneous composition.

The adduct obtained in the process according to the invention is separated from the precipitated dispersion in a customary manner, for example by decanting, filtering or centrifuging, and is washed or left unwashed, according to further processing. The water it contains is largely removed, for example by compressing it. In this way it is possible, for example, to obtain a product which contains about 30% by weight of polysaccharide besides about 7 % by weight of amine, the remainder being essentially water.

The products of the process can be separated into the polysaccharide and the amine by known methods, for example in accordance with U.S. Pat. No. 3,928,316, and they thus serve as starting materials for obtaining the free polysaccharides. On the other hand, the products are directly suitable for use as thickeners for a wide variety of applications. For instance, the adducts obtained according to the invention, unlike xanthan, become solvated in lower alcohols, in particular methanol, and form a gel, and they can therefore be used as thickeners for alcohols. The invention therefore also relates to the adducts themselves as well as to their use as thickeners.

In many applications it is advantageous to use the adducts moist, since the properties of the products can change on drying, which can substantially reduce the solvability and swelling.

The moist adducts also swell in aqueous solutions of many salts, such as sodium chloride, sodium sulfate, sodium phosphate, potassium chloride, calcium chloride, ammonium chloride, ammonium bromide, ammonium sulfate ammonium carbonate, ammonium formate, ammonium acetate or ammonium nitrate, and in some cases dissolve to some extent. It is also possible to use aqueous solutions of salt mixtures, for example a solution containing 13% by weight of sodium chloride as well as 1% by weight of calcium chloride.

In the examples which follow, the percentages are percentages by weight.

The xanthan fermentation solution used in the examples was obtained as follows:

The production strain used was Xanthomonas campestris NRRL B-1459. An agar culture in a glucose/peptone medium was transferred to the initial culture, and incubated therein at 30° C. in a shaker. This culture was used as the inoculum (3%) for a 10 liter fermenter the nutrient medium of which contained 3–5% of glucose or sucrose, 0.15–0.25% of cornsteep, 0.1 to 0.2% of sodium nitrate, 0.1% of dipotassium phosphate and 0.05% of magnesium sulfate hydrate. The inoculated fermenter was kept at 28° C., and aerated with stirring (400 rpm) at a rate of 10 liters of air/min. After about 36 hours, the fermentation medium contained 18–20 g of xanthan per liter.

EXAMPLE 1

10 g of coconutalkyldimethylamine (approximate carbon chain distribution: $C_{10}2$; $C_{12}57\%$; $C_{14}23\%$; $C_{16}11\%$; $C_{18}7\%$) was stirred to 1 liter of fermentation solution containing 20 g of xanthan. The dispersion formed was slowly added, also while stirring, to a mixture of 100 ml of deionized water and 25 ml of 2N acetic acid, and the adduct precipitated in the form of small stringy flat cakes, adduct formation in the interior of the cakes being incomplete at first but becoming complete on further stirring, as indicated by the pronounced shrinkage of the precipitate. The adduct was filtered off, and washed with deionized water, and its entrained water was removed in a filter cloth in a basket press. The press cake thus obtained, in addition to 35–40 g of water, also contained 20 g of xanthan and about 5.4 g of amine. The moist product was insoluble in deionized water, but dissolved to some extent in an aqueous solution which contained 19% of sodium chloride and 1% of calcium chloride. The adduct swelled strongly in this solution.

EXAMPLE 2

0.85 g of tallowalkyldimethylamine (carbon chain distribution in the tallowalkyl radical: about 5% of $C_{14}$; 30% of $C_{16}$; and 65% of $C_{18}$) was stirred into 100 g of a xanthan solution having a polysaccharide content of 1.8%. 2.5 g of 2N acetic acid were added, the dispersion obtained was coagulated, and the adduct was precipitated in the form of initially markedly swollen flat cakes which rapidly became desolvated on further stirring. The adduct was filtered off, and washed with deionized water, and the water was removed by pressing. This gave 6.2 g of a moist press cake which contained 1.8 g of xanthan and 0.43 g of amine.

EXAMPLE 3

Example 2 was repeated, except that the amine used was 0.85 g of soybeanalkyldimethylamine (carbon chain distribution in the soybeanalkyl radical; about 2% of $C_{14}$, 15% of $C_{16}$, and 83% of $C_{18}$). This gave 6.4 g of a moist press cake which contained 1.8 g of xanthan and 0.46 g of amine.

EXAMPLE 4

Example 2 was repeated, except that the amine was replaced by 0.85 g of stearylmethylethylamine and the acetic acid by 3 g of 2N lactic acid. This gave 6.2 g of a moist press cake which contained 1.8 g of xanthan and 0.47 g of amine.

We claim:

1. A xanthan adduct of an amine of the fomula $NR^1R^2R^3$ in which $R^1$ is alkyl having 10 to 20 carbon atoms, and $R^2$ and $R^3$, which are identical or different, denote methyl or ethyl.

2. An adduct of a heteropolysaccharide formed by fermentation of bacteria belonging to the genus Xanthomonas and an amine of the formula $NR^1R^2R^3$ in which $R^1$ is alkyl having 10 to 20 carbon atoms, and $R^2$ and $R^3$, which are identical or different, denote methyl and ethyl.

* * * * *